United States Patent [19]

Finarov

[11] Patent Number: 5,333,052
[45] Date of Patent: Jul. 26, 1994

[54] METHOD AND APPARATUS FOR AUTOMATIC OPTICAL INSPECTION

[75] Inventor: Moshe Finarov, Rehovot, Israel
[73] Assignee: Orbotech Ltd., Yanne, Israel
[21] Appl. No.: 796,954
[22] Filed: Nov. 25, 1991
[30] Foreign Application Priority Data
Nov. 27, 1990 [IL] Israel .................... 96483
[51] Int. Cl.⁵ ............................ G01N 21/21
[52] U.S. Cl. ................................ 356/369
[58] Field of Search ............ 356/364, 365, 366, 367, 356/369

[56] References Cited
U.S. PATENT DOCUMENTS

| | | | |
|---|---|---|---|
| 4,508,832 | 4/1985 | Carter et al. | 356/364 |
| 4,695,162 | 9/1987 | Itonaga et al. | 356/369 |
| 4,701,052 | 10/1987 | Schoen | 356/369 |
| 4,792,227 | 12/1988 | Yoshizawa | 356/367 |
| 4,866,264 | 9/1989 | Biricik et al. | 356/369 |
| 4,906,844 | 3/1990 | Hall | 356/369 |
| 5,076,696 | 12/1991 | Cohn et al. | 356/369 |

Primary Examiner—Richard A. Rosenberger
Attorney, Agent, or Firm—Benjamin J. Barish

[57] ABSTRACT

An inspection system for providing high contrast images of two materials of an article to be inspected is disclosed. Light with variable spectral range and large angular coverage is passed from the source through a polarizer, reflects from or is transmitted through the article to be inspected, passes through an analyzer and is detected by a sensor. A phase compensator is disposed either between the polarizer and the sample or the sample and the analyzer. Two of the three polarization optical components, that is, the polarizer, the compensator and the analyzer, are separately adjusted until the maximum contrast is found in the image. This enables high contrast imaging of surfaces of objects of similar optical reflectivity, (such as surfaces consisting of two similar specular materials, or surfaces partly covered with transparent films) which cannot be imaged using normal reflective image forming techniques. The system of the invention can also be operated to measure the thickness or index of refraction of transparent thin films.

36 Claims, 10 Drawing Sheets 5,333,052

METHOD AND APPARATUS FOR AUTOMATIC OPTICAL INSPECTION

FIELD OF THE INVENTION

The present invention relates to a method and apparatus for automatically optically inspecting articles. The invention is particularly applicable to the optical inspection of printed circuit boards (PCBs), multi-chip modules (MCMs), integrated circuits (ICs), reticle qualifications (RQs), flat panel displays (FPDs) of different types and the like for defects. The invention is also particularly applicable for measuring the thickness or index of refraction of thin film structures. The invention is therefore described below with respect to both such applications.

BACKGROUND OF THE INVENTION

In optical inspection of articles having surfaces of two or more materials, such as the articles mentioned above, a surface of the article is illuminated with light, and the image of the illuminated surface is collected by a light sensor and analyzed for defects. Various types of systems are known for this purpose.

One known type of optical inspection system, particularly useful for inspecting epoxy fiberglass substrates having metal conductors printed thereon, is based on the difference in fluorescence between the substrate and the conductors, to provide high contrast in the image of the two materials. Typical substrate materials fluoresce under appropriate illumination, appearing bright, while the metal pathways which do not fluoresce appear dark in the imaging system. However, this type of optical inspection cannot be used to distinguish between two non-fluorescing materials, such as two metal layers, or to image a thin insulating film on a metal layer which does not fluoresce because of its composition or thinness.

Another type of optical inspection system is based on the differences in reflectivity of the two materials. However, this type of system is not effective where the materials have similar reflectances.

A further type of known optical inspection system is based on a modification of the reflectivity system described above. In this system, the contrast between the two materials in the image is improved responsive to difference in their ability to preserve the polarization state of incident light. This method utilizes a pair of polarizers, one between the source and the object, and the other between the object and the detector. By using the relative orthogonal orientation of the polarizers, it is possible to obtain reasonable contrast between certain combinations of low reflectance materials, such as diffusely-surfaced (i.e. nonspecular) metals or laminates. However, this type of system cannot readily distinguish between two materials having the same or similar characteristics with respect to the preservation of the polarization state of incident light.

OBJECTS OF THE INVENTION

An important object of the present invention is to provide an automatic optical inspection method and apparatus producing an image having high optical contrast between the materials of the article inspected, whether or not their surfaces have similar reflectances.

Another object of the invention is to provide an automatic optical inspection method and apparatus which is not unduly sensitive to non-uniformity in the thickness of a film to be inspected, or to other parameters of the inspected surface.

A further object of the invention is to provide an automatic optical inspection method and apparatus including automatic optimization of the optical characteristics of the imaging system before the inspection process itself is performed.

A still further object of the invention is to provide a method of automatically optically measuring the thickness or index of refraction of a thin film structure.

SUMMARY OF THE INVENTION

According to one aspect of the present invention, there is provided an "ellipsometric" method of optically inspecting an article particularly a thin film multilayer structure including at least two materials. As is conventional, the article is illuminated with light, the light reflected from the article is collected by a light sensor, and the light collected by the light sensor is analyzed for defects. However, according to the invention, the light source is a source of intense polychromatic light. Also, a polarizer is disposed in the optical axis between the source and the object for linearly polarizing the incident light. The incident light thus has a "P-plane" component of polarization, parallel to the plane of incidence of the light on the article, and an "S-plane" component perpendicular to the P-plane component. An analyzer, comprising a second polarizing sheet, is disposed in the optical axis between the object and the sensor. A phase compensator is disposed either between the polarizer and the object, or between the object and the analyzer, for compensating for the phase shift between the P-plane component and the S-plane component caused by reflection from the materials of the surface. Finally, devices are provided for rotating the polarizer, the analyzer and the phase compensator about the corresponding optical axes to obtain the maximum contrast in images of the two materials collected by the sensor.

Instruments referred to as "ellipsometers", which are more particularly described below, are known for measuring the index of refraction of films and the thickness of films. Such instruments rely on the change of the polarization state after reflection of polarized light from such films responsive to their indices of refraction and thicknesses. Since the indices of refraction of most materials are known or can be measured, the measurement of the index of refraction of a material by an ellipsometer may also be used for identifying the material. However, the present inventor is aware of no suggestion in the prior art that the maximum contrast between two materials, as determined employing the above-described ellipsometric techniques, might be employed for optical inspection of articles for defects with strict requirements of such an inspection for a wide spectral range and large angular coverage of illumination light as well as for high uniformity of said illumination in the large observed area, as provided by an important aspect of the present invention.

In most applications of the present method of inspection of articles, the surface of the article to be inspected is reflecting, and therefore the optical axis between the source and sensor would include a reflection at its surface. However, in some cases the article to be inspected may be transparent, in which case the optical axis would pass through the article.

According to a further feature of the method of the invention, the maximum contrast between two materials of a surface of an object to be inspected is obtained by rotating two of the three devices (polarizer, analyzer and phase compensator) around corresponding optical axes, while maintaining the position of the third device constant. These "polarization optical devices" are thus rotated until the minimum intensity of the polarized light reflected from one material and the maximum intensity of polarized light reflected from the other material are detected, that is, until the contrast is maximized.

The process of the invention also includes variation of one or more additional parameters in order to obtain maximum contrast in the ellipsometric image. These parameters include the central wavelength of the light emitted by the source, the spectral bandwidth of the light, and the angle of incidence and the angular coverage of the incident light.

As will be described more particularly below, by utilizing ellipsometric contrast according to the invention, rather than conventional reflecting contrast, in an optical inspection system, the contrast in the image to be analyzed for defects can be increased up to two orders of magnitude (100-fold) or more.

A further advantage of the method of the invention is that the contrast in the image is relatively insensitive to non-uniformity in the thickness of the inspected film, and to certain other parameters of the inspected surface.

According to another aspect of the present invention, there is provided a method of automatically measuring the variation of thickness or index of refraction of a thin film structure. The preselected point of inspected structure is illuminated by intense polychromatic light of wide spectral range, light reflected from the structure is collected by a sensor, and the grey level signal of the image is measured. According to the invention, the incident light passes through a linear polarizer, so as to have a "P-plane" component parallel to the plane of incidence of the light, and an S-plane component perpendicular to the P-plane. An analyzer device is disposed in the optical axis between the object and the sensor, and a phase compensator device is disposed in the optical axis between the polarizer and analyzer for compensating the phase shift between the P-plane component and the S-plane component caused by the thin film structure. At least two of the polarizer, analyzer and phase compensator are rotated about the optical axes to obtain a minimum grey level signal. During inspection, the grey level signal obtained from different selected points is measured to produce an indication of the thickness or index of refraction of the thin film structure.

The invention also provides apparatus for optically inspecting articles for defects, and/or for optically measuring the thickness or index of refraction of a thin film structure, in accordance with the above ellipsometric method.

Further features and advantages of the invention will be apparent from the description below.

BRIEF DESCRIPTION OF THE DRAWINGS

The invention is herein described, by way of example only, with reference to the accompanying drawings, wherein.

DETAILED DESCRIPTION OF THE INVENTION

1. Null-Ellipsometry and Ellipsometric Contrast

Before describing the method and apparatus according to the invention for optically inspecting articles, which are based on obtaining maximum contrast by the use of ellipsometric techniques, it will be helpful first to describe the basic principles of ellipsometry in general, of null-ellipsometry, and of ellipsometric contrast.

A. Ellipsometry

Ellipsometry is defined as a method for optical measurement of changes in the polarization state of light reflected from a surface being investigated.

Figure 1:
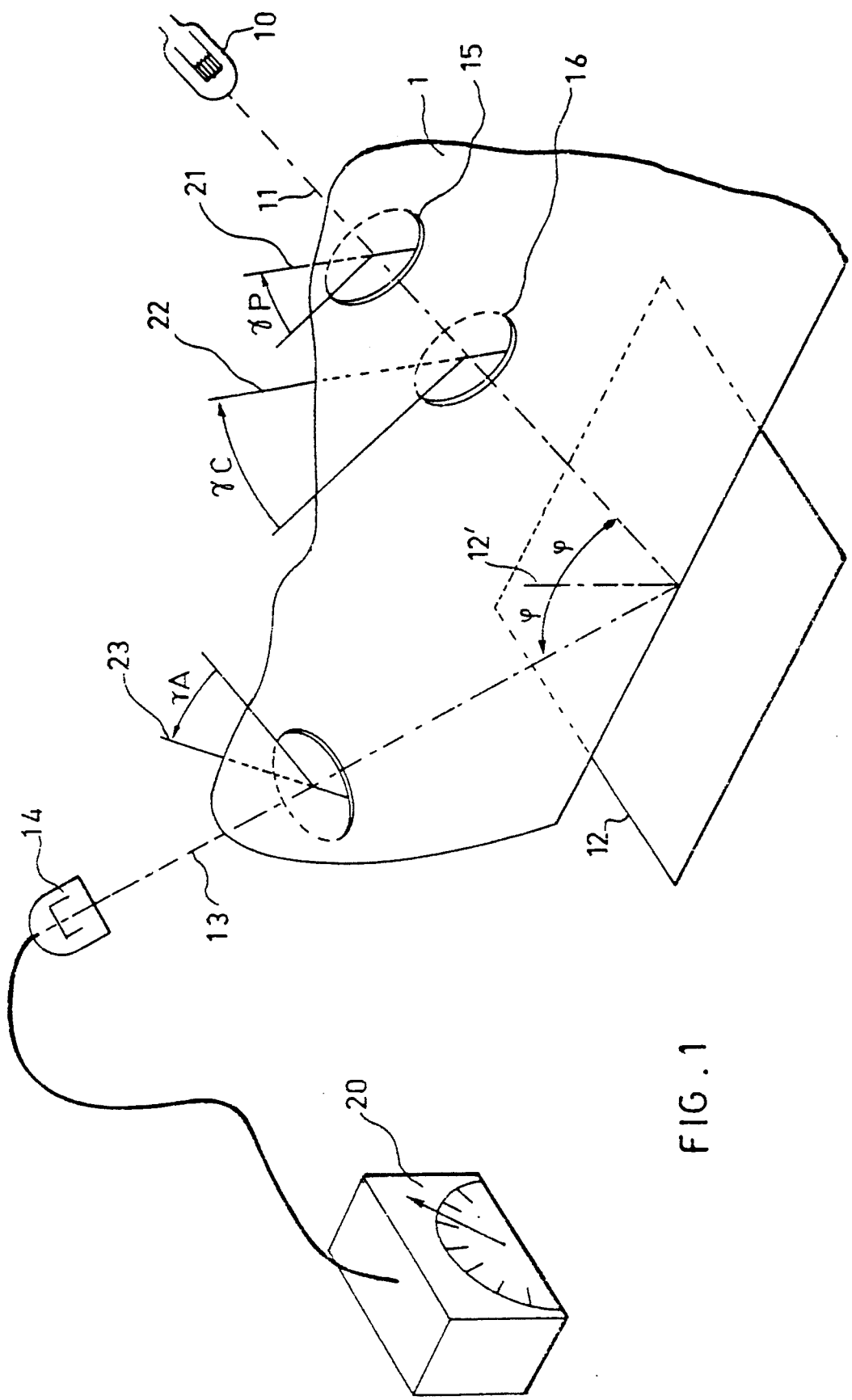
FIG. 1 is a diagram illustrating the operation of a null ellipsometer, which will be helpful in better understanding the present invention.

Certain terms and definitions used in ellipsometry, and herein, are illustrated in FIG. 1. The change of polarization state of light reflected from a surface is defined by two factors: (1) the "amplitude factor", $\psi$, that is, the ratio of the change of the amplitude $E_p$ of the P-plane component (the component polarized parallel to the plane of incidence of the light), to the change of the amplitude $E_s$ of the S-plane component (the component perpendicular to the plane of incidence) of the electric field strength vector $\bar{E}$ of polarized incident light; and (2) the "phase" factor, $\Delta$, which is the phase shift between the phase changes of P- and S-plane components. In FIG. 1, the P-plane contains the incident beam with an optical axis 11, the reflected beam with an optical axis 13, and the normal 12' to the investigated surface 12.

When a light beam of a given polarization state is reflected from a surface, the polarization state of the reflected light beam commonly differs from that of the incident beam.

Quantitatively, the change of the polarization state is defined by two angles $\psi$ and $\Delta$ as follows:

$$\tan\psi = (E_p{}^r/E_p{}^i)/(E_s{}^r/E_s{}^i) \qquad (1)$$
$$\Delta = (\delta_p{}^r - \delta_p{}^i) - (\delta_s{}^r - \delta_s{}^i)$$

wherein: E and $\delta$ are amplitude and phase, respectively, of vector $\vec{E}$; p and s refer to the type of polarization component; and i and r refer to incident and reflected light beams.

The difference in polarization states of the incident and reflected beams depends on the properties of the reflecting surface, which properties are described by the Fresnel general complex reflectance coefficients ($\tilde{R}_p$, $\tilde{R}_s$) for the P- and S-components, respectively.

The ellipsometric equation establishes the relation between the optical properties of the object, described by $\tilde{R}_P$ and $\tilde{R}_S$, which may be calculated, and the changes in the polarization state, defined by $\psi$ and $\Delta$, which can be measured.

The basic ellipsometric equation is as follows:

$$\tan(\psi) \cdot \exp(i\,\Delta) = \tilde{R}_P/\tilde{R}_S, \text{ where } i = \sqrt{-1} \qquad (2)$$

Commonly used ellipsometric methods deal with relatively smooth surfaces (such as polished or sputtered metal) and semiconductor substrates, or like surfaces covered with one or more thin transparent layers. The optical properties of such objects are defined by the refractive index (n), and absorption coefficient (k) of the substrate, and by the refractive indices and the thicknesses (d) of all the transparent layers (k=0). In the simplest example, e.g., a clean metal substrate, the Fresnel coefficients depend only on the values of n and k of the substrate.

Designating tan $(\psi)\cdot\exp(i\Delta)=\tilde{p}$, for a given wavelength $\lambda$ and angle of incidence $\phi$, the basic ellipsometric equation becomes simple enough:

$$\tilde{p} = \frac{\cos\left[\phi + \arcsin\left(\frac{\sin\phi}{n - ik}\right)\right]}{\cos\left[-\phi + \arcsin\left(\frac{\sin\phi}{n - ik}\right)\right]} \qquad (3)$$

The solution of Eq. (3) is:

$$\psi = \arctan |\tilde{p}|, \quad \Delta = \arg(\tilde{p}). \qquad (4)$$

For example, for incident light defined by $\lambda=0.63$ $\mu$m and $\phi=70°$, the ellipsometric parameters of aluminum (n=1.5, k=7.4) and silicon (n=3.85, k=0.02) are:
Al : $\psi=41.58°$, $\Delta=143.03°$
Si : $\psi=10.34°$, $\Delta=179.16°$ In the case of a substrate covered with one or more thin films, the calculation of the Fresnel coefficients is more complicated. For example, for a one-layer reflecting structure:

$$R_P = \frac{\tilde{R}_{P1,2} + \tilde{R}_{P2,3} \cdot \exp(-2i\delta)}{1 + \tilde{R}_{P1,2} \cdot \tilde{R}_{P2,3} \exp(-2i\delta)} \qquad (5)$$

$$R_S = \frac{\tilde{R}_{S1,2} + \tilde{R}_{S2,3} \cdot \exp(-2i\delta)}{1 + \tilde{R}_{S1,2} \cdot \tilde{R}_{S2,3} \exp(-2i\delta)} \qquad (6)$$

where $\tilde{R}_P$ and $\tilde{R}_S$ are the Fresnel coefficients for reflection at the boundary between the i- and (i+1)—media.

For a thin transparent layer on a substrate, medium i=1 is the ambient air ($n_1=1$, $k_1=0$), medium i=2 is a transparent film ($n_2=n_f$, $k_2$ 0, $d=d_f$) and medium i=3 is the substrate ($n_3=n_s$, $k=k_s$).

Parameter $\delta$ (the phase shift), caused by an interference in the transparent film, is expressed by the formula:

$$\delta = \frac{2\pi d_f}{\lambda} \sqrt{n_f^2 - \sin^2\phi} \qquad (7)$$

Even for a one-layer structure it is difficult to obtain an analytical solution of the ellipsometric equation, and its solution therefore usually calculated by computer. The result of such a calculation may be illustrated by a graph of the angles $\psi$, and $\Delta$ as functions of the optical parameters, for example $n_f$ and $d_f$.

Figure 2:
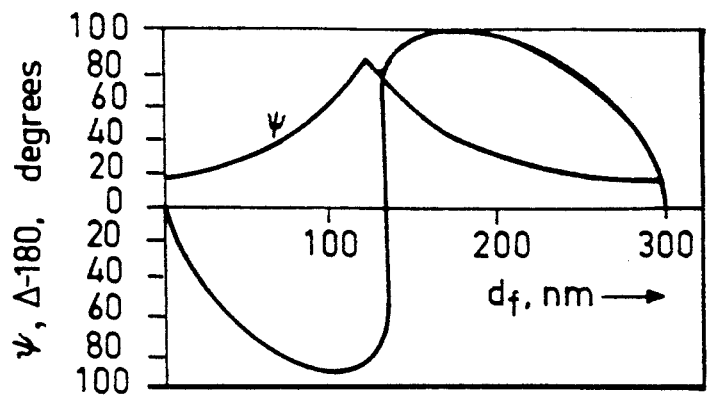
FIG. 2 is a diagram illustrating the dependence of the ellipsometric parameters $\psi$ and $\Delta$ on the thickness $d_f$ of a thin transparent silicon dioxide film on an opaque silicon substrate, measured at an angle of incidence of 70° and with light of 632.8 nm wavelength.

FIG. 2 illustrates a graph of the ellipsometric parameters ($\psi$, $\Delta$) as functions of the thickness $d_f$ of a transparent film on a silicon substrate. It will be observed that the ellipsometric parameters $\psi$ and $\Delta$ differ radically at substantially all values of the film thickness. For example, at a film thickness of $d_f\approx 0$ (clean silicon substrate), $\psi\approx 10°$ and $\psi\approx 179°$; but for a film thickness of $d_f\approx 50$ nm, $\psi\approx 40°$ and $\Delta\approx 100°$.

Such drastic differences in the ellipsometric parameters of two reflecting structures, for example, a substrate having two different thicknesses of a transparent film thereon, occur even though the optical reflectance of the surface is essentially similar. This fact is exploited by the present invention and is employed in creating a high contrast image system for an optical inspection method and apparatus.

B. Null Ellipsometry

Null ellipsometry is one method of measurement of ellipsometric parameters. A null ellipsometry system is illustrated in FIG. 1. It includes a light source 10 illuminating an article 12 to be investigated along an optical axis 11. Reflected light is collected at the end of an optical axis 13 by a light sensor 14. The plane of incidence I includes the optical axes 11 and 13, as well as the normal 12' to the surface of the inspected article 12.

FIG. 1 illustrates three principal optical components of the polarization optical system, namely a polarizer 15, a phase compensator 16, and an analyzer 17. The phase compensator 16, which is usually a quarter-wave plate, may be in either the optical axis 11 or the optical axis 13.

According to the null ellipsometry method, at least two of these three polarization optical components and their optical axes 21, 22 and 23, respectively, are selectively rotated about the corresponding axes 11 and 13 while maintaining the third component stationary. At some position, a minimum reflected light intensity will be received by the sensor 14, that is, the reflected light will be "extinguished" Rotation of the above three polarization optical components 15, 16 and 17 is schematically shown in FIG. 1 as being effected by a polarizer motor $M_P$, an analyzer motor $M_A$, and a compensator motor $M_C$, respectively. The light collected by the sensor 14 is measured by a measuring device 20.

The reflected light intensity measured by the sensor 14 depends on the characteristics of the reflecting surface 12 and angular positions $\gamma_A$, $\gamma_P$, $\gamma_C$ of the three polarization optical components with respect to the plane of incidence 1. By rotation of the polarization optical components, their positions in which the output beam is "extinguished," i.e., is of minimum intensity, can be achieved. In this condition, the ellipsometric parameters $\psi$ and $\Delta$ can be calculated from the above-mentioned angular positions of the three components.

For example, in the "PCSA" arrangement (i.e., in which the polarization optical elements are in following order: polarizer, compensator, sample, analyzer, as in FIG. 1), with a fixed compensator, one of four equivalent extinguishing states is:

$$\gamma_C = 45°; \psi = \gamma_A; \Delta = 2\gamma_P + 90° \qquad (8)$$

If the null ellipsometer is adjusted to the extinguishing state, i.e. providing the minimum output for a specific specimen, any change in the angular position of any one of these components, (that is, variation of any of $\gamma_A$, $\gamma_P$ or $\gamma_C$) will increase the intensity of the reflected light beam.

In the PCSA arrangement, with $\gamma_C = 45°$ (i.e., when the compensator is a perfect quarter-wave plate), the relation between output and input intensities (I and $I_0$ respectively) may be expressed as follows:

$$I/I_0 = \left( \frac{|\tilde{R}_P|^2 + |\tilde{R}_S|^2}{2} \right)(1 - \cos 2\psi \cdot \cos 2\gamma_A + \qquad (9)$$

$$\sin 2\psi \cdot \cos\Delta \cdot \sin 2\gamma_A \cdot \sin 2\gamma_P - \sin 2\psi \cdot \sin\Delta \cdot \sin 2\gamma_A \cdot \cos 2\gamma_P)$$

C. Ellipsometric Contrast

According to the invention, the fact that $I/I_0$, according to Eq.(9), varies over a wide range is exploited to yield very high contrast in images of surfaces consisting of two different materials. That is, $I/I_0$ is adjusted to as nearly as possible to zero with respect to one of the two materials. Then, as the ellipsometric parameters for essentially all materials of interest vary greatly, $I/I_0$ for the other material will in substantially all cases be much greater than zero. The method of the invention may also be used to image variation in the thickness of a transparent thin film, as the ellipsometric parameters vary substantially with film thickness. Accordingly, the resultant image exhibits high contrast between the two materials.

For example, if the article consists of two specular surfaces, one of aluminum and the other of silicon, and the polarization parameters are adjusted such that the beam reflected from the aluminum is essentially extinguished ($\psi_{A1} \approx 41.58° \Delta_{A1} \approx 143.04$, $\gamma_A \approx 41$ $58°$, $\gamma_P \approx 26.52°$, $I/I_0 \approx 0$), the intensity of the light reflected from the silicon surface will be $I/I_0 \approx 0.3$. If it is assumed that system noise (caused by imprecision in the optical components, presence of depolarized light in the output flux, non-uniformity of the reflecting surface, and the like) can be kept as low as $10^{-3}$, the ellipsometric light intensity contrast ratio provided according to the invention between these materials will be approximately 300. This is more than two orders of magnitude better than the contrast between the reflectivity of the same materials to visible light. When the specular substrate is silicon or aluminum or the like, and is compared to the same substrate covered with a thin transparent film, the ratio between the null ellipsometric contrast and the reflective contrast is even greater.

2. Description of the Preferred Embodiments

Overall Optical Inspection System

Figure 3:
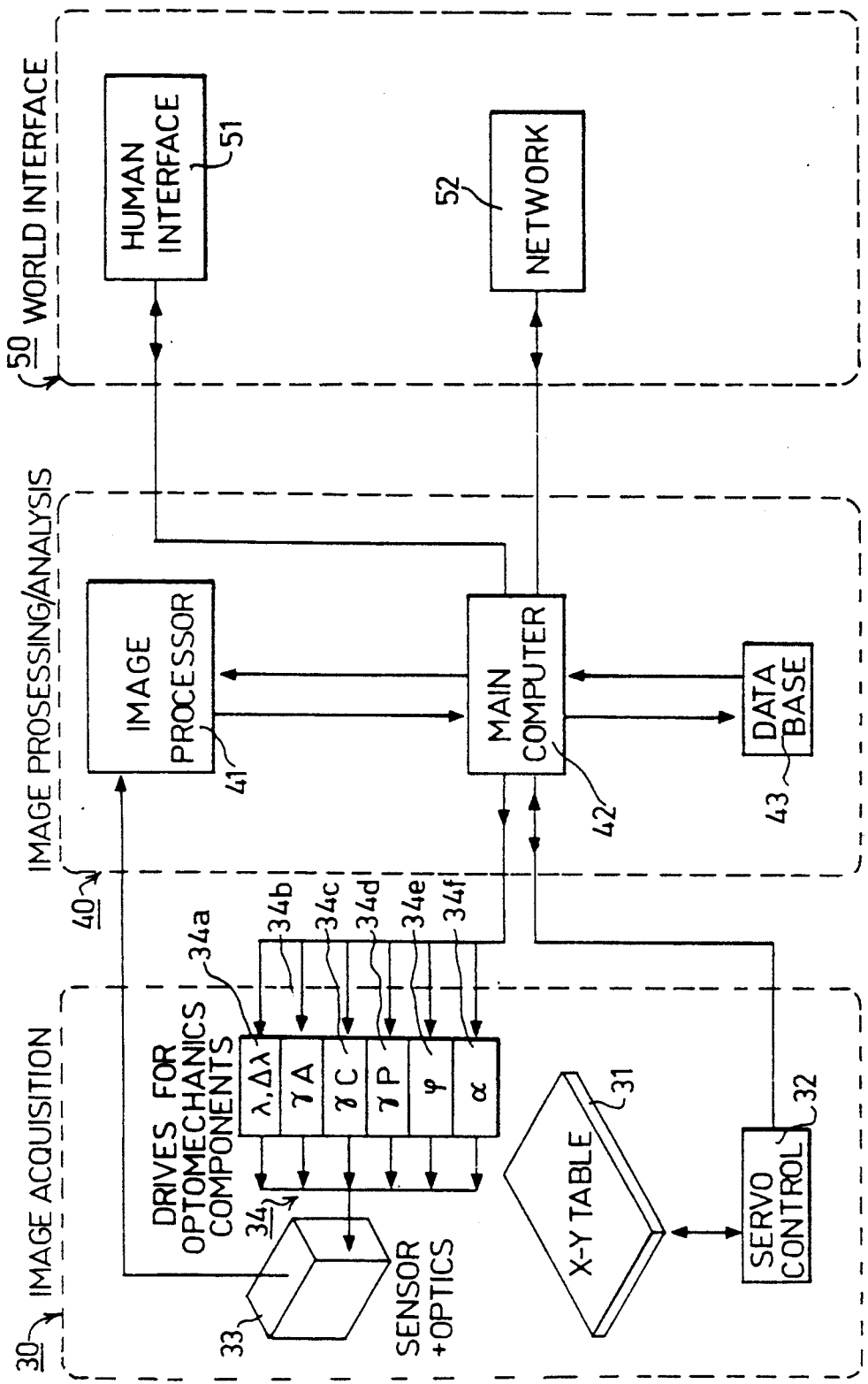
FIG. 3 is a block diagram illustrating one form of optical inspection system in accordance with the present invention.

FIG. 3 illustrates the main components of an optical inspection system in accordance with the present invention. Such a system includes three main subsystems, an image acquisition subsystem 30, an image processing and analysis subsystem 40, and a world interface subsystem 50.

The function of the image acquisition subsystem 30 is to illuminate the inspected area and to transform the optical image to electric signals transmitted to an image processor 41 in the image processing and analysis subsystem 40. The image acquisition subsystem 30 includes an X-Y table 31 holding the inspected article and driven by a servo control unit 32 controlled by the main computer 42 of the image processing and analysis subsystem 40. The image acquisition subsystem 30 further includes an optical head 33 that contains a light source, a sensor, and optics for illuminating and imaging the article on the X-Y table 31. The sensor in the optical head 33 may be a linear-array sensor, such as a linear charge-coupled-device (CCD) sensor or time-delay integration (TDI) sensor, whereupon the article would be scanned in a continuous manner; alternatively, the sensor in the optical head 33 could be a planar-array sensor, such as a CCD or Vidicon, whereupon the article would be scanned in a step-by-step manner.

Optical head 33 includes control circuitry 34 for driving the mechanical devices which according to the invention displace the optical components to achieve the optimal ellipsometric contrast in the particular article inspected. The control circuitry 34 is controlled by the main computer 42 in the image processing and analysis subsystem 40, and physically moves the optical components to vary the respective parameters until maximum ellipsometric contrast is obtained. Schematically, this control circuitry 34 may be considered to include circuitry 34a, for selecting the central wavelength ($\lambda$) of the light source, and the width of the spectral range ($\Delta\lambda$); circuitry 34b, for selecting the optimum rotational angle of the analyzer ($\gamma_A$); circuitry 34c, for selecting the optimum rotational angle of the compensator ($\gamma_C$); circuitry 34d, for selecting the optimum rotational angle of the polarizer ($\gamma_p$); circuitry 34e, for selecting the optimum angle of incidence ($\phi$); and circuitry 34f, for selecting the optimum angular coverage ($2\alpha$).

The image processing and analysis subsystem 40 includes, in addition to the image processor 41 and main computer 42, a database 43, which stores the parameters for maximum null ellipsometric contrast of the materials of the articles to be inspected. The image processor 41 processes the image signals supplied by the sensor in the optical head 33 in order to recognize and analyze features of the article being inspected, such as lines, pads and the like in the case of printed circuit boards. The analysis may comprise both comparison of the features of the image to stored features or may involve so-called "design rule" comparison. Image processing is performed in a real time manner, concurrently with image scanning. Preferably, dedicated hardware and software is used in the image processing and analysis subsystem 40 to provide high speed processing of the image data.

The world interface subsystem 50 includes a human interface unit 51 and a network interface unit 52. The human interface unit 51 preferably includes a keyboard for inputting information, a display for displaying information, a printer for outputting a "hard copy" of the processed information, and the like. The network interface unit 52 may be connected to an external computer for inputting information into the main computer 42. Either interface unit may be used for inputting the appropriate information into the main computer 42 to enable it, together with the data stored in the database 43, to control the image acquisition system to obtain maximum null ellipsometric contrast for each particular article to be inspected.

Figure 3A:
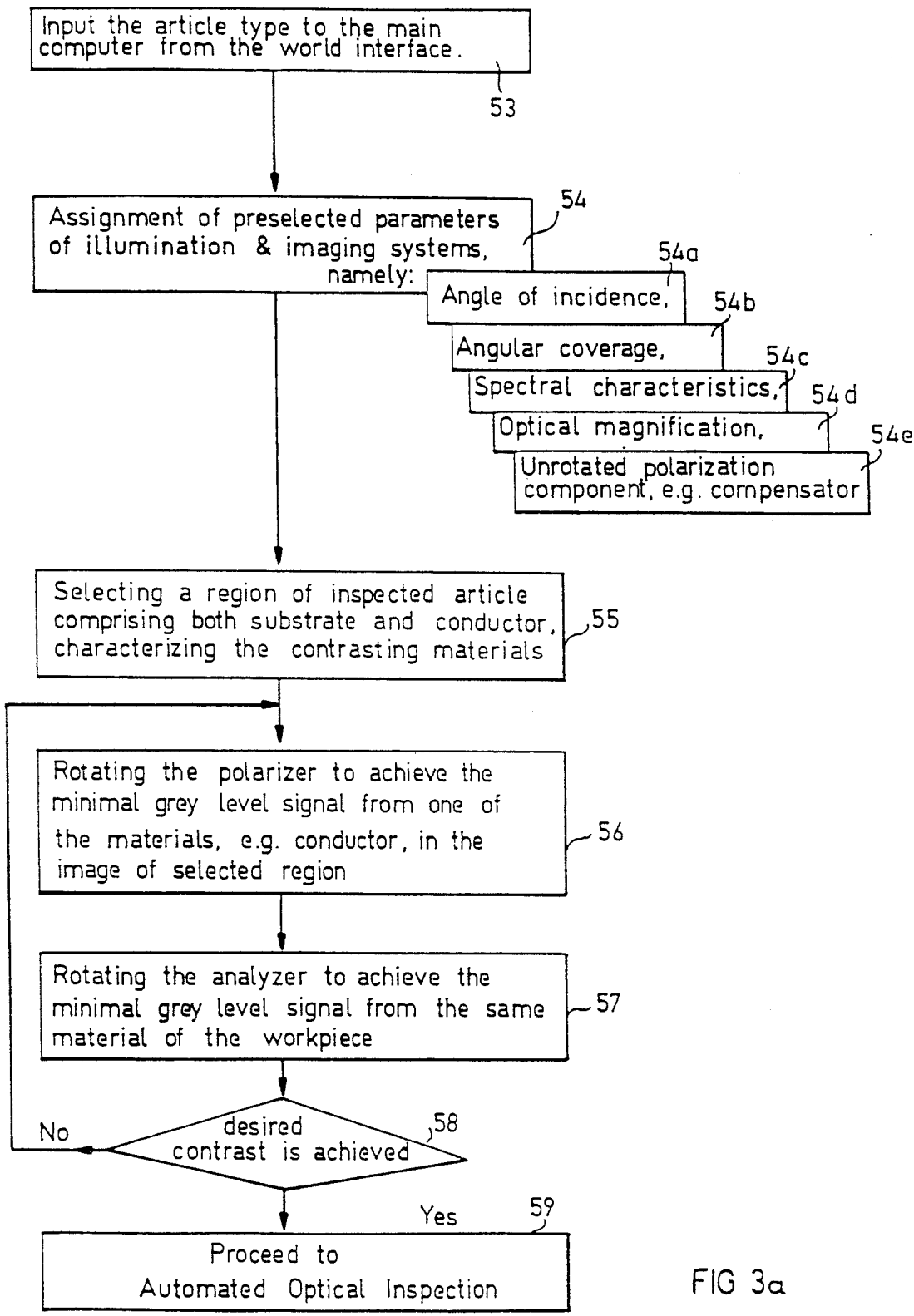
FIG. 3a is a flow chart illustrating one procedure for setup of the optical inspection system of the present invention before proceeding with the actual automated inspection process.

FIG. 3a is a flow chart illustrating typical operation of the system of FIG. 3. More particularly, FIG. 3a illustrates the manner in which the inspection parameters are selected by the system in order to maximize the ellipsometric contrast between the various materials of an article to be inspected, after which it may be used for optically inspecting the article for defects.

First, in step 53 the article type (i.e. the materials of the surface to be inspected, and any "design rule" data or the like) is input to the main computer, for example, from the human interface 51 (FIG. 3). In step 54, preselected parameters are then assigned, namely the angle of incidence (step 54a), the angular coverage (step 54b), the spectral characteristics (step 54c), the optical magnification (step 54d), and the identification of the polarization component which is not to be rotated (step 54e). These parameters can be provided by the operator via the human interface, or can be selected from the database, having been stored responsive to earlier examination of objects comprising similar materials.

A region of the inspected article is then selected for examination in step 55. In the case of a PC board or the like, this section would comprise both substrate and conductor, characterizing the contrasting materials. The polarizer (for example) is then rotated in step 56 to achieve the minimal grey level signal from one of the materials, e.g., the conductor, in the image of the selected region; and the analyzer is then rotated in step 51 to further reduce the minimal grey level signal from the same material.

A decision is then made (step 58) whether the desired contrast has been achieved. If not, steps 56 and 57 are repeated. When the desired contrast has been achieved, the system proceeds to an automated optical inspection procedure, according to the particular inspection system involved. As noted, for the purposes of the present invention, the automated optical inspection process itself is generally conventional.

Examples of the Optical Head

Figure 4:
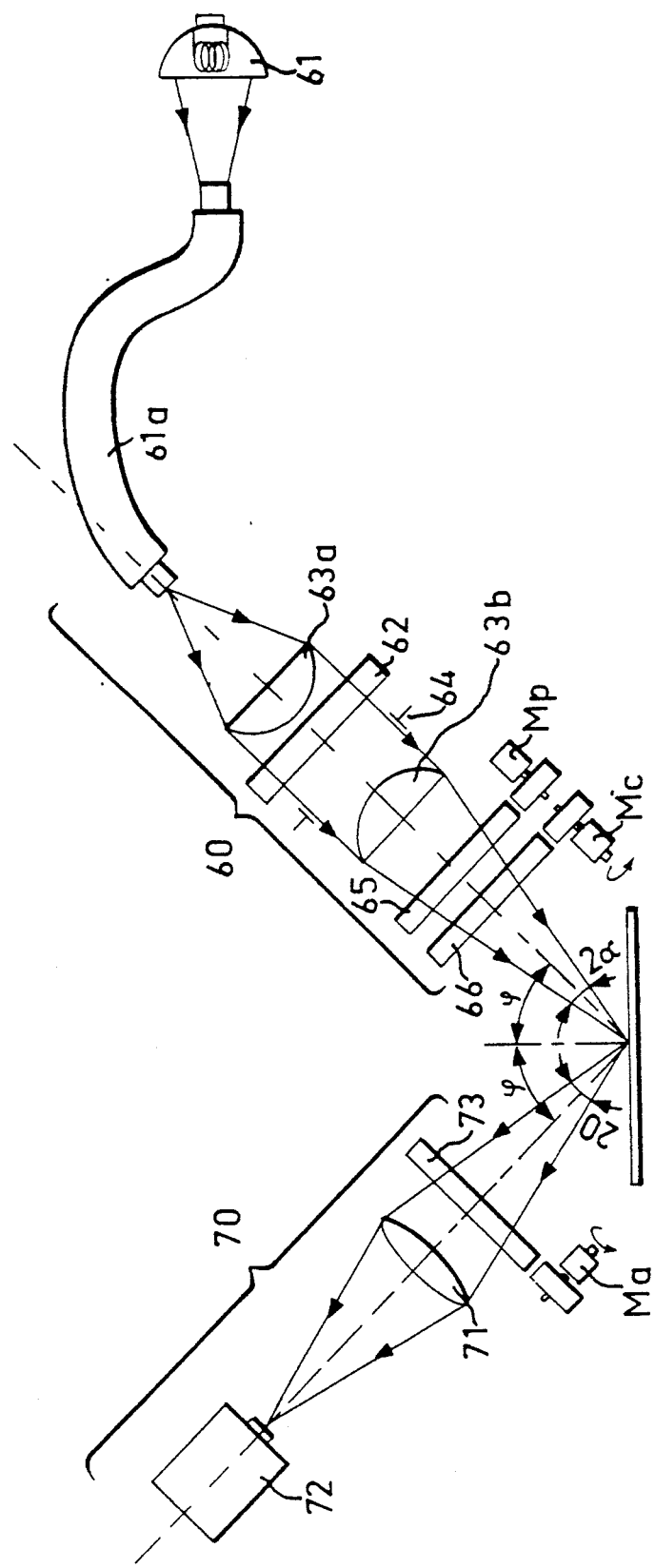
FIG. 4 more particularly illustrates the optical head in the system of FIG. 3.

FIG. 4 diagrammatically illustrates one form of optical head 33 which may be used in the system according to the invention to perform the steps of FIG. 3a. The optical head includes an illumination system, generally designated 60, and a light collecting or imaging system, generally designated 70.

The illumination system 60 includes a light source 61 of intense polychromatic light of wide spectral range, such as white light, and a variable spectral filter or a set of spectral filters 62. The illumination system 60 further includes an optical fiber assembly 61a and standard optic components, such as condensing lenses 63a and 63b, and aperture stop 64, all designed according to the specific requirements of the inspection system, for focusing the light on the surface of the article 12 to be inspected.

The light collecting system 70 is in the reflected light path of the optical head and includes an imaging lens 71 and a sensor 72 which collects light reflected from the article 12 being inspected.

The foregoing elements are generally conventional in optical inspection systems, and therefore further details of these elements are not set forth. According to one aspect of the invention, however, these components and those which control the ellipsometric contrast in the image are preferably mounted on optical arms, shown schematically at 69a and 69b. These arms are rotatable about an axis normal to the axis of incidence and coincident with the plane to be inspected on the surface of the object to be inspected, such that the angle of incidence $\phi$ can be varied to optimize the ellipsometric contrast, as necessary.

In order to achieve maximum ellipsometric contrast in the light collected from the article 12 to be inspected, the illumination system 60 includes a linear polarizer 65, and the light collecting system 70 includes an analyzer 73. In addition, one of the two systems includes a phase compensator 66. This is shown in FIG. 4 in the illumination system 60, but it will be appreciated that the phase compensator 66 could also be disposed in the light collecting system 70, that is, in the reflected light path.

As described earlier, according to the invention, two of the parameters of the optical system are pre-selected for every specific type of article to be tested, or may be optimally adjusted responsive to the control circuitry 34 (FIG. 3), in order to obtain maximum null ellipsometric contrast. These are the angle of incidence ($\phi$) and the angle of coverage ($2a$).

The angle of incidence ($\phi$) is controlled by control circuitry 34e (FIG. 3) according to the specific properties of the inspected surface in order to obtain maximum ellipsometric contrast. The ellipsometric contrast is maximal when the angle of incidence ($\phi$) is close to the Brewster angle (for dielectric substrates) or the pseudo-Brewster angle (for metal substrates). This suggests that the angle of incidence ($\phi$) should be relatively near the horizontal. On the other hand, increase in the angle of incidence ($\phi$) increases the sensitivity of the image to any lack of flatness of the local surface to be inspected, increases distortion in the dimension of features on the substrate in the plane of incidence, and reduces the depth of focus of the illuminator.

The angular coverage ($2a$) is defined by the half-angle ($\alpha$) of the light cone which illuminates the imaged area of the surface to be inspected. The required angle of coverage depends on the angular aperture of imaging lens 71 in the light collecting system 70, and on the physical "slopes" of the features of the inspected surface 12 relative to the plane of the inspected surface, that is, for example, on the angle at which the "sides" of conductors printed on a substrate meet the plane of the substrate.

The optimal angular coverage ($2a$) also depends on the characteristics of the surface to be inspected, and may be controlled by a driver 34f (FIG. 3) controlling the aperture of a diaphragm 64 (FIG. 4). If the surface is highly specular and flat, the angular coverage must at least equal the aperture of the imaging lens 71, to provide for maximal spatial resolution of the imaging system. The desired angular coverage also depends on the topography, i.e., the relief of the inspected surface. On the one hand, the greater the possible curvature of the inspected surface, e.g., the greater the roughness of the surface, the greater angular coverage desired, as in any brightfield imaging system. On the other hand, a large angular coverage leads to complications in the optical design of the illumination system as well as of the light source.

The spectral distribution $\Delta\lambda$ of the light is another important characteristic of the illuminator and of the entire image acquisition system. When different materials and thin film structures are to be inspected, usually it would be preferable to use an intense white light source, such as a quartz-tungsten-halogen lamp, a xenon high pressure arc lamp, or the like. These produce high brightness over a wide spectral range, usually wider than that of the sensor sensitivity. For example, a silicon CCD sensor provides good performance only in the range of 400–800 nm.

When the inspected surface is composed of opaque materials, for example gold-on-copper, aluminum-on-silicon, or the like, high ellipsometric contrast may be achieved by using light of a wide spectral range, even white light including the entire visible spectrum. This is because the optical parameters of these materials, in particular the ellipsometric parameters $\psi$ and $\Delta$, are substantially constant over a wide range of the visible spectrum.

Figure 5A:
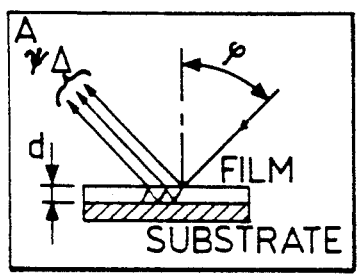
FIGS. 5a, 5b and 5c are diagrams illustrating the influence of the spectral bandwidth of the incident light on the ellipsometric contrast.
Figure 5B:
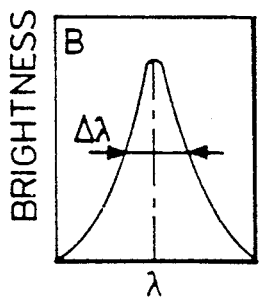
Figure 5C:
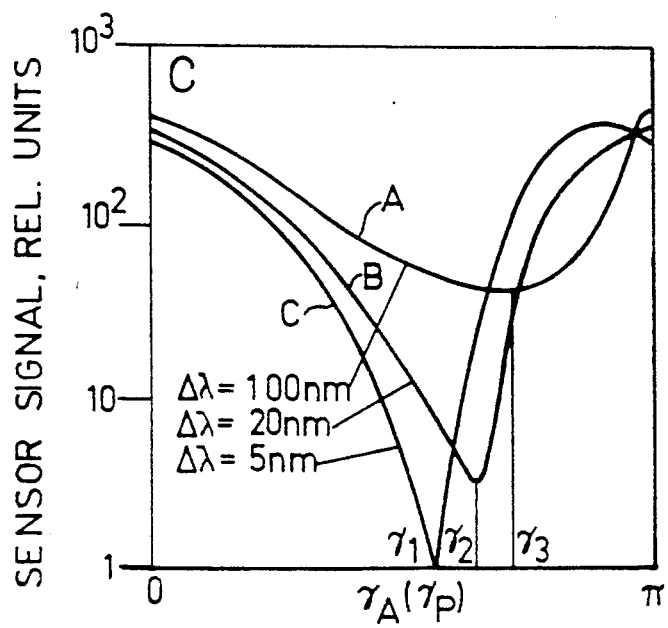

When at least one of the components of the inspected article is a specular substrate covered with a thin transparent film, the dependence of the ellipsometric contrast on the spectral characteristics of the illuminating light is more complicated. This is particularly illustrated in the diagrams of FIGS. 5a, 5b and 5c. Because of multiple reflections of light which take place in such films as illustrated in FIG. 5a, for every wavelength in a given spectral range $\Delta\lambda$ (FIG. 5b), there is a definite set of ellipsometric parameters $\psi$ and $\Delta$. The $\psi$ and $\Delta$ angles of the optical structure for the whole spectral range may also be calculated and measured variation in $\psi$ and $\Delta$ is an approximate function of the spectral bandwidth $\Delta\lambda$ (FIG. 5b). Thus, for curve A in FIG. 5c, in which $\Delta\lambda = 100$ nm, as indicated, the minimum intensity achieved in the null ellipsometric procedure is not as sharply defined as when monochromatic or narrow band light sources are used, as illustrated by curves B and C of FIG. 5c, wherein $\Delta\lambda$ is 20 nm and 5 nm, respectively. Similarly, as shown by FIG. 5c, use of a narrow band source provides more complete extinguishment of the light. Thus, noise in the image can be reduced by reducing $\Delta\lambda$, the spectral bandwidth.

Consider the case where one material of the inspected article is a bare metal layer, and another is a metal substrate covered with a transparent film. If it is assumed that the ellipsometric parameters of the optical system are adjusted according to the invention so that the light reflected from the substrate is extinguished (i.e., is dark in the image), the bare metal layer image then is bright, If monochromatic light is used for this inspection, very high contrast of the image responsive to these surfaces may be obtained. On the other hand, any spatial non-uniformity of film thickness leads to non-uniformity in the image (optical noise). In some inspected surfaces, if there are substantial differences between the actual and nominal film thickness, and if the $\psi$ and $\Delta$ parameters of the substrate may be similar to those of the bare metal layer, the contrast between them may disappear.

The solution to the latter problem is to use non-monochromatic light and inverse contrast. In this case, the ellipsometric parameters are adjusted, according to the method of the invention, so that the image of the metal layer is extinguished, that is, so that the metal layer is dark in the image. The substrate thus will be bright in the image, because light of a relatively wide spectrum is now being used. In this case, the $\psi$, $\Delta$ parameters of the substrate and respective grey level signal in the image do not strongly depend on the film thickness variations (as illustrated by curve A, FIG. 5c), and therefore the image would have both high contrast and uniformity.

Therefore, it is an important aspect of the practice of the present invention that, for every specific thin film structure to be inspected, the spectral characteristics ($\lambda$, $\Delta\lambda$) of the illuminating light are chosen to obtain the optimal image contrast and uniformity. Light of a relatively wide spectral range will usually be preferable, to provide maximum brightness of the available illumination, allowing faster scanning of the inspected area. Accordingly, if a white light source is used in the illuminator, a set of different filters, or a variable spectral filter, as shown at 62 in FIG. 4, may be used. In practice of the invention, the parameters $\lambda$ and $\Delta\lambda$ are controlled by the main computer 42 (FIG. 3) via the control circuitry 34b.

As shown in FIG. 4, the light collecting portion 70 of a system according to the invention, located along the optical axis of the reflected light, consists principally of the imaging lens 71, the sensor 72, and the analyzer 73. The imaging lens 71 images the illuminated surface of the article 12 being inspected (which is in the object plane) onto a photo-sensitive area of the sensor 72 (which is in the image plane).

In automatic optical inspection scanning systems, a linear-array sensor, such as a linear CCD, is usually used as the sensor 72. Such a sensor produces an electrical signal proportional to the intensity of the respective spot of the image for each picture element or "pixel" along a line imaged on the object being inspected. The spatial resolution is generally defined by the optical magnification and resolution of the lens 71 and the performance of the sensor 72.

The linear array sensor moves in a precisely controlled way relative to the X-Y table 31 (FIG. 3) in the direction perpendicular to its surface. Thus, the line is effectively moved along the object by physical motion of the optical head with respect to the object. High spatial resolution is achieved using this inspection arrangement, while obtaining high efficiency of the illumination system, since only a narrow strip of the surface need be illuminated. However, the scanning speed of a linear-array sensor (e.g., a linear CCD) is limited in that a definite minimum integration time is required by each photosensitive element of the sensor, i.e., the element corresponding to each pixel of the image.

To increase the scanning speed and, accordingly, to reduce the inspection time, a TDI (Time Delay Integration) sensor may be used. Such a known sensor, which consists of a planar array of light sensitive elements, scanned in a step-by-step manner, permits collection of electric charge responsive to light detected from the object in several parallel line arrays of the sensor. In effect, the same line on the surface of the article is sequentially scanned a number of times. The main physical limitation of the TDI sensor is reduction of the modulation transfer function (MTF) as compared to a simple line-array sensor. The MTF is effectively reduced due to object-to-sensor oscillations caused by mechanical vibration.

As described earlier, at least three polarization optical devices are employed in the system of the invention in order to obtain maximum ellipsometric contrast. These three devices, as shown in FIG. 4, are the linear polarizer 65, the compensator 66, and the analyzer 73. Polarizer 65 is a linear polarizer producing linearly polarized light having a P-plane component, that is, parallel to the plane of incidence of the light, and an S-plane component, perpendicular to the P-plane. Compensator 66 compensates for the phase shift between the P-component and S-component of the reflected polarized light. Analyzer 73, when adjusted with its polarization plane perpendicular to the polarization plane of the "compensated" reflected light, is effective to extinguish the reflected light.

Different types of compensators 66 may be used. A mica or liquid crystal quarter-wave plate is preferred, because these materials have the best tolerance to beam angle divergence or convergence and absorbs minimal light in the spectral range of interest.

The polarizer 65 and the analyzer 73 may also each be of several types, including prisms, dichroic sheets, and the like. Prism polarizers provide the best extinguishing ratio (the ratio between the intensities of light beams passed through parallel polarizers and crossed polarizers). However, such prism polarizers are difficult to incorporate in suitable optical systems. Dichroic sheet polarizers and analyzers are preferable as their use simplifies system design. Such sheet-like devices are relatively tolerant to the angle of divergence and convergence of the illuminating/reflected beams, and to the spectral distribution of the radiation, induce minimal aberration in the illumination and imaging systems, have significantly smaller dimensions, and are easy to align and rotate.

A disadvantage of the optical arrangement illustrated in FIG. 4 is that all the polarization optical components are located close to the inspected article, so that both the imaging lens and the illuminator optics must be provided with large working distances. This makes it difficult to form high magnification images, for example, with the aid of microscope objectives. Another disadvantage is that the location of the polarization optical components in the short conjugate sides of the optical axis (i.e., between the condenser lens 63b and the object 12 on the illuminating side, or between the object 12 and the collecting lens 71 on the sensing side) means that the light passing through these components is converging or diverging, which degrades their performance. An arrangement in which the light passes straight through the polarization optical components is preferable.

Figure 6:
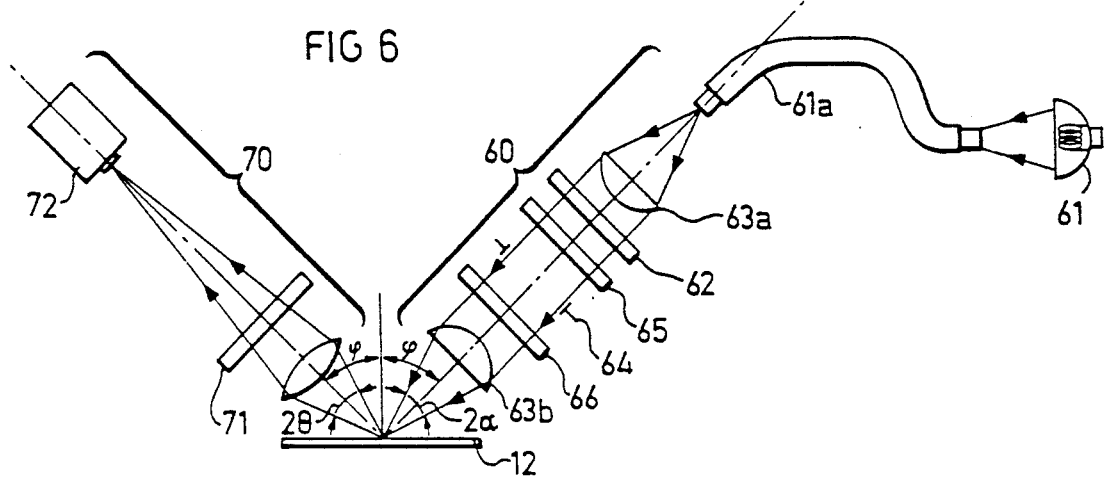
FIG. 6 is a diagram illustrating the optical head of the present invention in an embodiment in which the polarizer, compensator and analyzer are all located in the long conjugate side of the illuminating and imaging systems.

FIG. 6 illustrates another arrangement of the invention which addresses this problem. In this case, the polarizer 65 and compensator 66 are incorporated in the long conjugate side of the illuminating system 60, that is, between the lenses 63a and 63b of the condenser, and the analyzer 73 is incorporated in the long conjugate side of the light collecting system 70 between lens 71 and the sensor 72. This arrangement avoids the disadvantages described above of the FIG. 4 arrangement, but requires the use of a condenser lens 63b in the illuminating system 60, as well as an imaging lens 71 in the light collecting system 70. Both are preferably formed of glass having reduced internal stresses, to avoid any possible birefringence which might influence the ellipsometric contrast.

Figure 7:
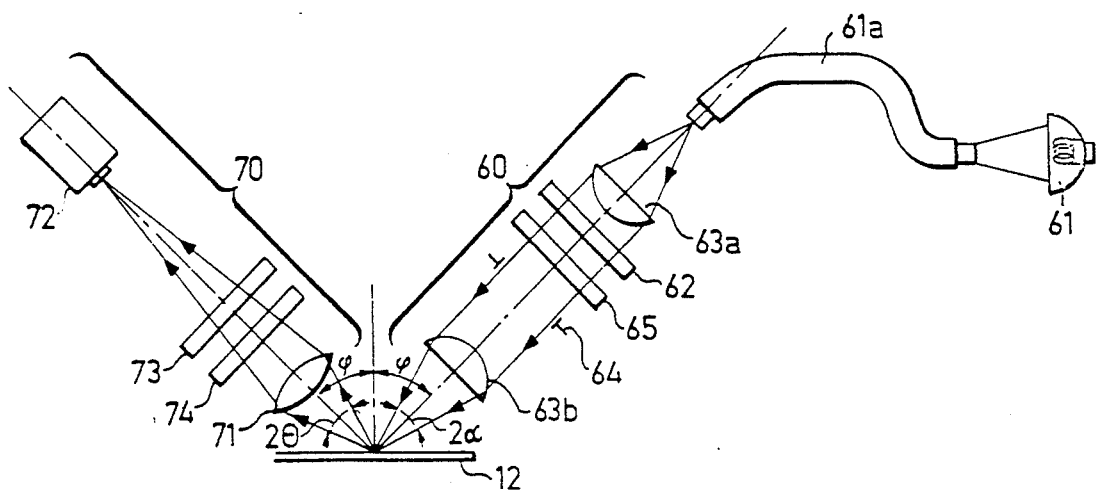
FIG. 7 is a diagram illustrating the same optical head as in FIG. 6 but wherein the compensator is located in the reflected light path.

It will be appreciated that the FIG. 6 arrangement could also include the compensator in the imaging system 70, rather than in the illuminating system 60; this alternative is illustrated in FIG. 7. Accordingly, the phase compensator 74 may be located in either the illumination system 60 or the imaging system 70. The former case is called a "PCSA" (Polarizer-Compensator-Sample-Analyzer) arrangement, whereas the latter is called a "PSCA" arrangement.

Whether a PCSA or PSCA arrangement is used does not influence the ellipsometric contrast; rather, the choice between the two arrangements depends principally on optical design constraints and performance considerations. For example, if the optical performance of the imaging system is critical, it is preferable to locate the compensator in the illuminating system, as shown at 66 in FIG. 4, so as to avoid any additional aberrations it might otherwise induce in the light collecting system of the reflecting light path 70. On the other hand, if the illuminated area is relatively large, requiring large optical components, and the light collecting system performance is not critical, or if the aberrations may be compensated for in the imaging lens design, it would be preferable to use the PSCA arrangement, wherein the compensator 74 is located in the light collecting system 70 of the reflected light path, as shown in FIG. 7.

It will also be appreciated that other modifications of the optical head may be suggested in order to tailor the above-described null ellipsometric technique to specific applications.

One such application is the inspection of flat display panels utilizing glass as a substrate and multiple thin films, some of which may be transparent in the visible light region. The basic optical scheme illustrated in FIG. 4 may be used for distinguishing different materials on the inspected article, but where transparent thin film structures are involved, the signal to noise ratio (SNR) will be low, due to the inherently low reflectances of those materials.

Figure 8:
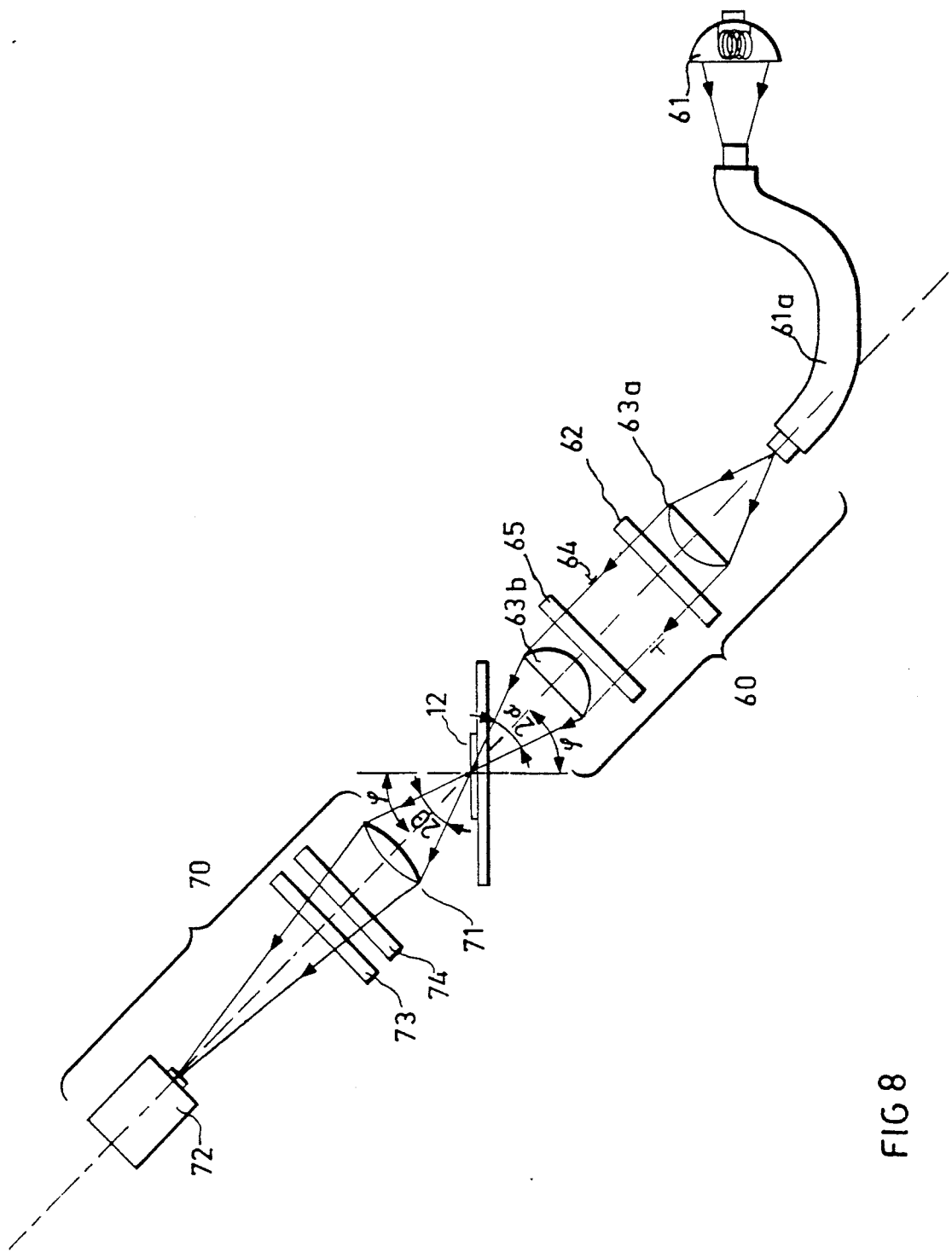
FIG. 8 is a diagram illustrating the arrangement of the optical system of the invention when the article being inspected is transparent.

FIG. 8 illustrates an arrangement that may be used for inspecting such transparent, low-reflectance articles. In the FIG. 8 arrangement, the components are the same as in the reflected light scheme, e.g., of FIG. 7, and are therefore identified by the same reference numerals, except that the illuminating system 60 is located to transmit the incident light through the transparent test article, and the light collecting system 70 is located on the opposite side of the inspected article. In both of these arrangements, the dark levels (the signals from the extinguished locations) will be approximately the same, but the bright level in the transmitted light arrangement of FIG. 8 will obviously be much greater than in the reflected light arrangement of FIG. 7.

In the transmitted light arrangement of FIG. 8, all the procedures for obtaining the maximum ellipsometric contrast would be the same as in the reflected-light arrangement (e.g., of FIG. 7); however, the basic ellipsometric equation (Equation 2 above) must be written in slightly different form:

$$\tan(\psi) \cdot \exp(i\Delta) = \tilde{T}_P / \tilde{T}_S \qquad (10)$$

where $\tilde{T}_p$ and $\tilde{T}_s$ are the Fresnel complex transmission coefficients of the inspected article. Reference herein and in the appended claims to reflective systems according to the invention should be understood to include such transmissive arrangements, where permitted by the context.

Figure 9:
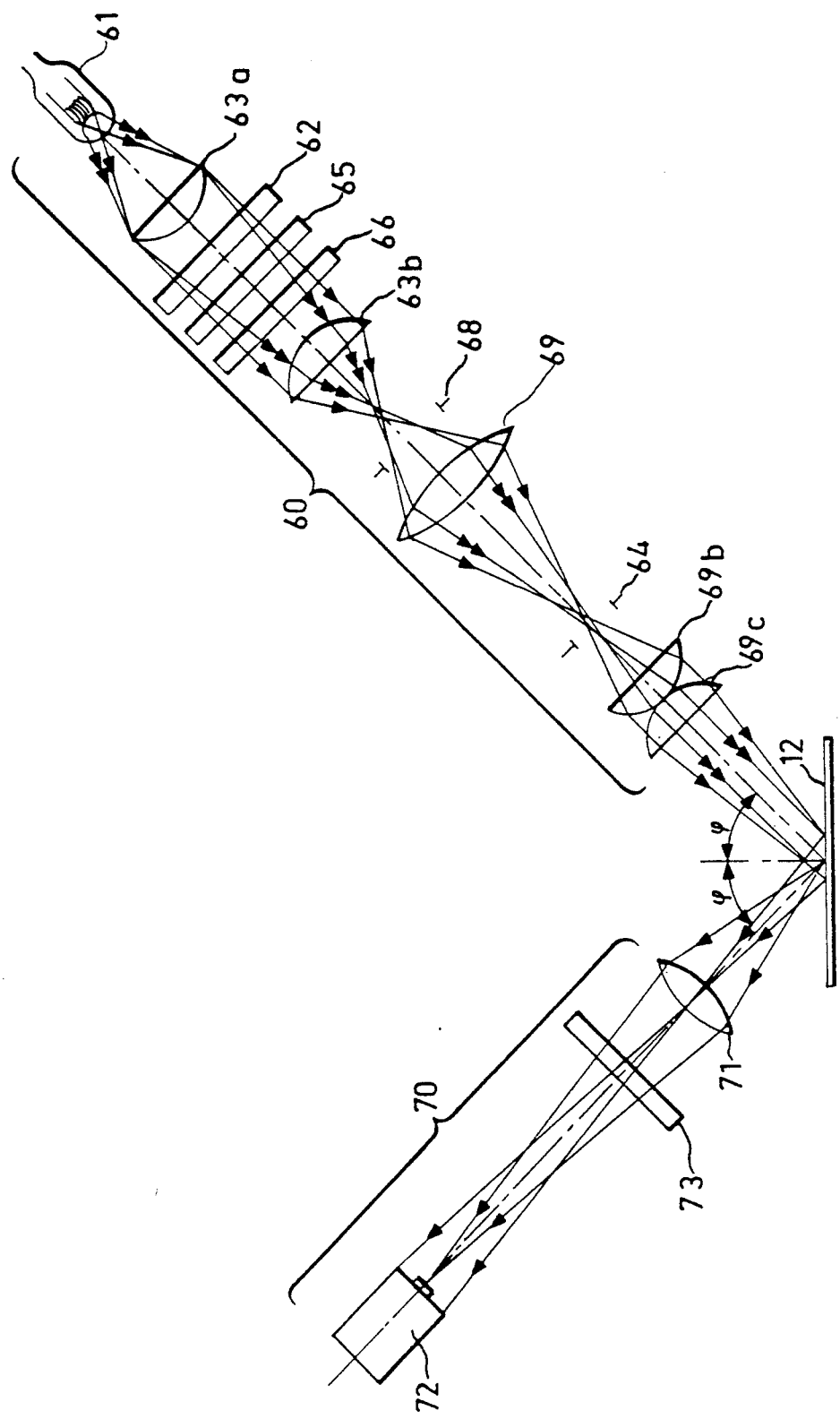
FIG. 9 is a diagram illustrating an optical head according to the invention, provided with a microscope type illuminator.

FIG. 9 illustrates an optical head arrangement which is similar to those already discussed, but using a microscope-type illuminator including a field stop 68 and lenses 69a, 69b, 69c. In other respects this embodiment of the invention is similar to those previously discussed.

When a planar-array or area sensor is used, such as a CCD matrix, the sensor may be scanned in a step-by-step manner. This mode of scanning is usually used in an automatic optical inspection system for verifying and displaying defects after detecting them. In such cases, the area sensor "looks" at the surface around the location of the defect to be verified with increased optical magnification. The verification may be carried out visually, e.g. using a high resolution video monitor, or automatically.

Figure 10:
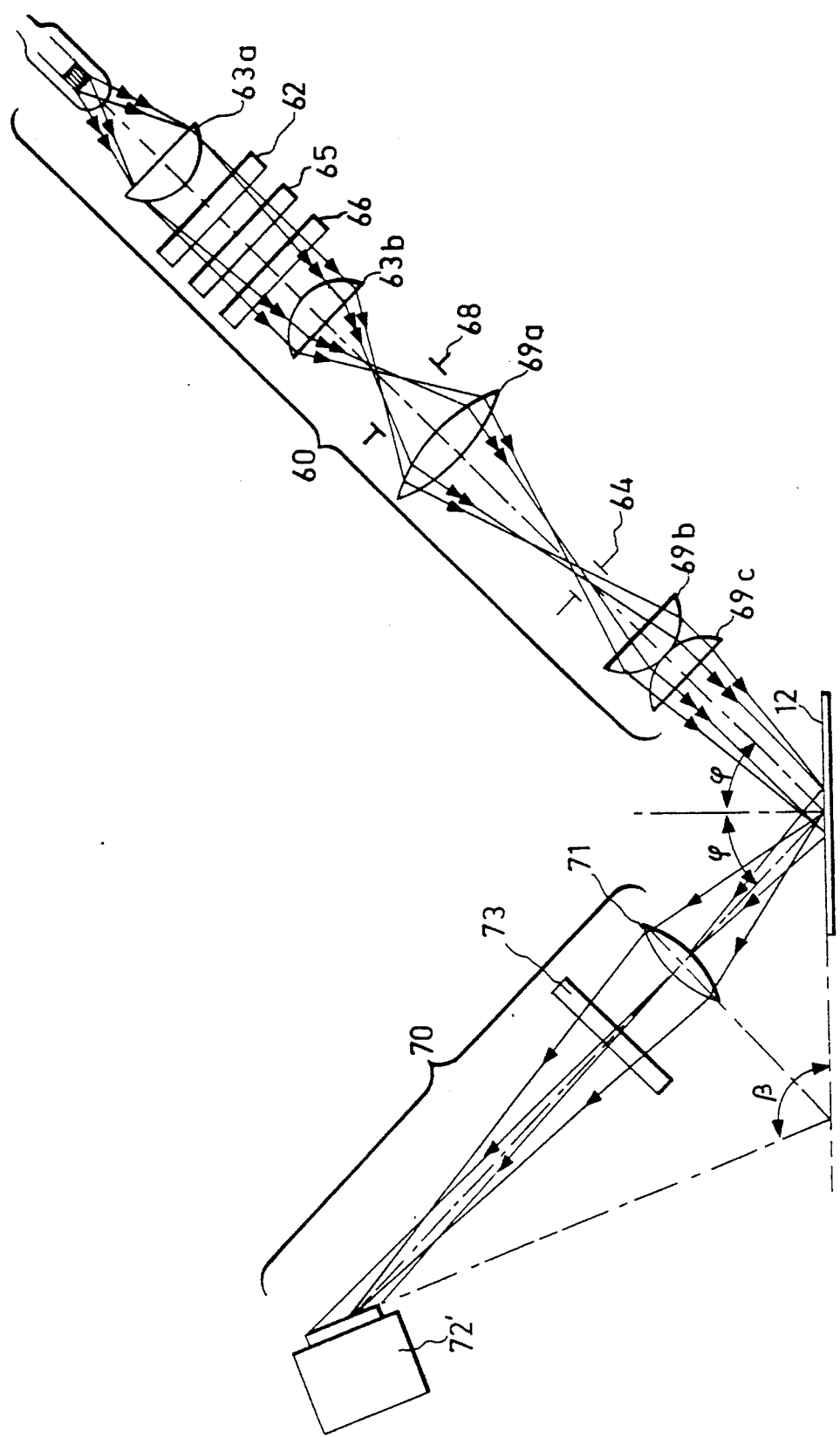
FIG. 10 is a diagram illustrating the optical head according to the invention, wherein the detector includes a planar array of light sensitive elements.

When an area sensor is used, it is necessary to incline the plane of the area sensor to the optical axis in order to produce clear images of the entire inspected surfaces at the sensor at any angle of incidence. This is illustrated in FIG. 10, wherein the optical arrangement is similar to that of FIG. 9, but the sensor 72' is an area sensor including a planar array of photosensitive elements. In FIG. 10, the plane of the area sensor 72' is inclined at an angle $\beta$ to the object plane 12. This angle may be calculated by the following relationship:

$$\beta = \phi + \arctan [M \cdot (\tan\phi)] \tag{11}$$

where "M" is the optical magnification of the imaging system.

Procedure of Extinquishing the Output Light Beam

As described earlier, according to the invention, in order to obtain maximum ellipsometric contrast in images of surfaces consisting of two different materials, at least two of the three polarization components (polarizer, compensator and analyzer) are rotated to extinguish the image (i.e., minimize the intensity) of one of the materials of the inspected article. Thus, there are the following three options:

A. The angular position of the polarizer is held constant, and the compensator and the analyzer are rotated. This option is preferable when, for example, a long narrow strip is to be scanned with a linear (CCD) camera, and the polarizer is too big to enable free rotation around the optical axis. The preferable angular position of the polarizer in this case is $\gamma_p = \pm 45$ degrees.

B. The angular position of the analyzer is held constant, and the compensator and the polarizer are rotated. This option is preferable if a prism polarizer is used as an analyzer, as during its rotation round the optical axis mechanical misalignments may cause the image of the object to move in the image plane as well as if a free distance of imaging lens does not allow location of analyzer rotating mechanism.

C. The angular position of the compensator is held constant, and the polarizer and the analyzer are rotated.

Rotation of two of the three components according to one of these three options is carried out according to the invention until one of the materials of the inspected article is extinguished in the image, or if neither of the materials is fully extinguished, until the maximum contrast between the compared materials is achieved.

This procedure may be carried out either manually or automatically. In both cases, the procedure is a consecutive, step-by-step rotation of each of two of the three polarization optical components in a limited angle range (for example, $0 \leq \gamma_A \leq \pi/2$ for the analyzer and $0 \leq \gamma_p \leq \pi$ for the polarizer, with $\gamma_C = \pi/4$ constant for the compensator), the minimum intensity of one of the materials in the image being achieved in each step. In each case, rotation of one component causes a previous minimum value (that is, a minimum determined with respect to the other component) to change, necessitating alternate adjustments of the two components to locate the maximal extinction of the reflected beam.

Figure 11A:
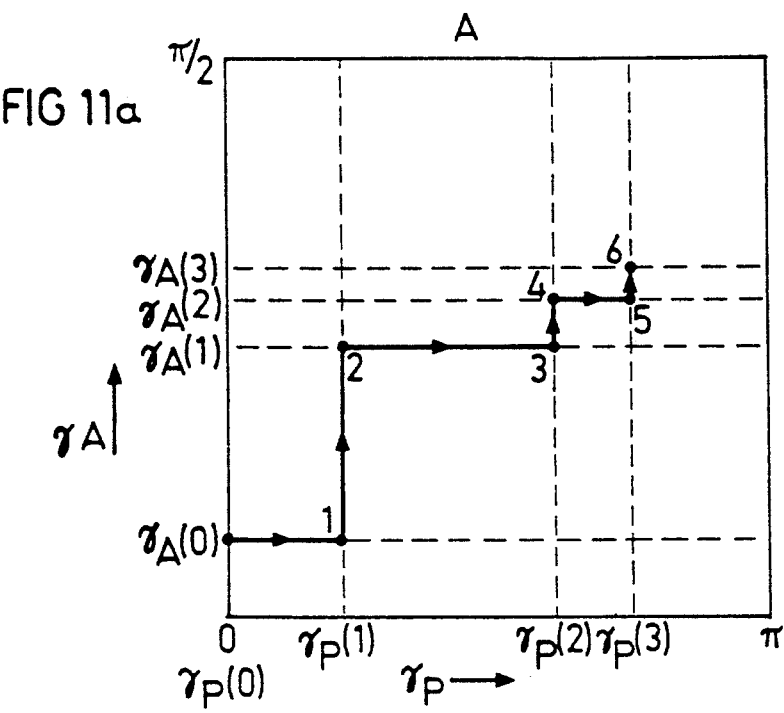
FIGS. 11a and 11b are diagrams illustrating the procedures for maximizing the ellipsometric contrast in images formed according to the present invention.

This procedure is illustrated in FIG. 11a for the PCSA arrangement with a fixed compensator.

The initial positions of the polarizer and the analyzer are termed: $\gamma_A^{(0)}$, $\gamma_p^{(0)}$. By rotating the polarizer in the range $0 \leq \gamma_p \leq \gamma$, a first local intensity minimum, point 1 (FIG. 11a) is determined, by noting the lowest signal in the image from one of materials of the object; the coordinates of this minimum are termed $\gamma_A^{(0)}$, $\gamma_p^{(1)}$. Keeping the angle $\gamma_p^{(1)}$ constant, the analyzer is then rotated in the range $0 \leq \gamma_A \leq \pi/2$, until the second local minimum of $\gamma_p$, point 2 (coordinates $\gamma_p^{(1)}$, $\gamma_p^{(1)}$) is found. Variation of $\gamma_p$, between 0 and $\pi$ is repeated, until a new minimum $\gamma_A^{(1)}$, $\gamma_p^{(2)}$ is located This loop may be repeated many times until the global minimum is achieved, e.g., point 6, $\gamma_p^{(3)}$, $\gamma_A^{(3)}$.

The criterion to determine when a global minimum has been achieved may be defined in different ways. For example, the global minimum signal may be defined to be less than a specified threshold. Another way is to define a maximum number of steps of local minimum searching as described above which will be carried out; or a combination of both conditions may also be used.

The process of determining a global minimum described above may be automated by programming the main computer 42 to control physical rotation of the polarization optical components to achieve successive local minima, as described above. However, certain known numerical methods of searching extreme values may also be employed.

Figure 11B:
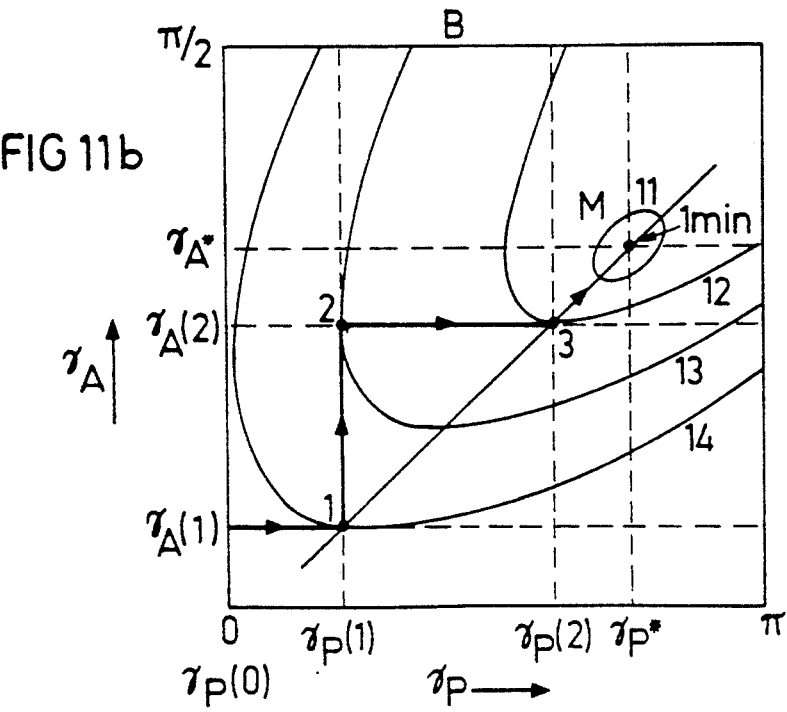

Specifically, a simple algorithm is illustrated in FIG. 11b for locating the global intensity minimum in a fast manner, based on the step-by-step search described earlier and the similarity of intensity as a function of angles and $\Delta$ to the square power type aim functions. In FIG. 11b, the generally similar curves shown are curves of equal intensity I, which has a global minimum value $I_{min}$ at the point M with coordinates $\gamma_P^*$, $\gamma_A^*$. Carrying out three steps of local minimum searching (0 --> 1 --> 2 --> 3) as above, the coordinates $\gamma_P^*$, $\gamma_A^*$ of the global minimum $I_{min}$ may then be found by simultaneously changing the angles of rotation $\gamma_A$ and $\gamma_p$ along a straight line passing the points 1 and 3 according to the equation:

$$\frac{\gamma_A - \gamma_A^{(1)}}{\gamma_A^{(2)} - \gamma_A^{(1)}} = \frac{\gamma_P - \gamma_P^{(1)}}{\gamma_P^{(2)} - \gamma_P^{(1)}} \tag{12}$$

Thus global minimum searching may always be completed in a maximum of four searching steps.

In some applications, when two thin film structures on a surface of an inspected article are to be compared, the films may not be of uniform thickness. In such cases, the minimum reflected light intensity level may be different in different places of the same structure, so that the optical system has to be automatically adjusted to the same global minimum in real time during the scanning process. This may be done by comparing the actual minimum detected at a particular point to the global minimum deviation, and using the result as a feedback parameter for the component control circuitry 34 (FIG. 3).

Real time feedback adjustment of the angular positions of the components, for example $\gamma_P$ and $\gamma_A$, may be carried out very effectively. If the relation between the film thickness and the ellipsometric parameters $\psi$, $\Delta$, has been previously calculated, the output intensity deviation as a function of film thickness at accepted nominal values of the angles $\gamma_P$ and $\gamma_A$ can be determined in accordance with Equation (9).

The procedure may also be performed vice versa. That is, by measuring the deviation of the intensity from the global minimum value, knowing the variation in relative intensity with variations of the film thickness from its nominal value, it is possible to evaluate thickness deviations along the inspected surface. This option is particularly useful for inspection of opened "windows" in a dielectric film (e.g., silicon dioxide) after its etching to the silicon substrate, in accordance with the dependence of the, $\Delta$ a parameters on film thickness as shown in FIG. 2. If the angles $\gamma_P$, $\gamma_A$ selected according to the invention are chosen with respect to the pure silicon, all the completely opened windows will be extinguished (black) in the image. If some of the windows are not completely etched, they will be bright and will be recognized as defects. Moreover, by measuring the relative intensity (grey level signal) in these places, it is easy to calculate the remaining film thickness in all such windows, and determine their statistical distribution.

According to this data the operator can decide if additional etching is desired, and if so, determine the required conditions of the process, e.g., the additional etching time.

The null ellipsometric technique of the invention thus provides not only high contrast images, but also allows in-process comparison of the "extinguished" signal to its global minimum value. This in turn permits evaluation of any deviations of the film thickness from its nominal value. Moreover, the area and the statistical distributions of such deviations can readily be calculated. This is very important information for process control.

Optical inspection according to the above-described ellipsometric contrast technique may be used as an independent inspection method, or may be used together with another inspection method, e.g., to verify the presence of a defect. Besides its ability to provide high contrast images, the ellipsometric inspection method has the additional advantage that it is possible to form another image using the inverse contrast. That is, in the process of the invention the polarization optical components are set to extinguish the signal from one material of the surface; it is possible to then reset those parameters to generate a second image in which the other material is extinguished, and compare the two images thus produced. In this way it is possible to distinguish between actual defects, such as shorts and opens, and such phenomena as local oxidation or contamination or surface slopes and the like, which produce intensity irregularities in the image but do not interfere with the proper function of the object.

Measuring Film Thickness or Index of Refraction

It will be appreciated that the method and apparatus described above can also be used for automatically optically measuring the thickness or index of refraction of a thin film structure. This is done using the apparatus described above to illuminate the structure with light, collecting the light leaving the structure by a light sensor, and measuring the grey level signal of the image. As above, a polarizer is employed for linearly polarizing the light incident on the sample to have a P-plane component parallel to the plane of incidence of the light, and an S-plane component perpendicular to the P-plane component. An analyzer device is disposed in the imaging path, and a phase compensator device is disposed in one of the paths for compensating the phase shift between the P-plane component and the S-plane component caused by reflection from inspected article.

In such a method and apparatus, the relative angular positions of the polarizer, analyzer and compensator devices are adjusted to obtain the minimum grey level signal, and the minimum grey level signal is measured. Such a measurement provides a direct indication of the thickness, and of the index of refraction, of the thin film structure.

The method of automatically optically measuring thickness or index of refraction of a thin film according to this aspect of the invention is otherwise similar to the steps performed in determining ellipsometric parameters, resulting in extinction of reflection from one of the surface materials before automatically inspecting an article for defects, as described above.

While the invention has been described with respect to several preferred embodiments, it will be appreciated that these are set forth for purposes of example only, and that many other variations, modifications and improvements on the embodiments of the invention disclosed above may be made. Therefore, the above specification is to be understood to be exemplary of and not limiting on the invention, which is to be limited only by the following claims.

What is claimed is:

1. A method of optically inspecting a surface of an article particularly a thin film multilayer structure including at least two materials, comprising the steps of:

illuminating the article with light from a light source, collecting the light leaving the article using a light sensor, forming an image responsive to light collected by the light sensor, and analyzing said images for defects, the improvement wherein the light source is a source of intense polychromatic light of wide spectral range; and wherein the method further comprises the following additional steps:

disposing a polarizer device in the optical axis between the source and the article, to linearly polarize the incident light to have a P-plane component parallel to the plane of incidence of said light, and an S-plane component perpendicular to the P-plane;

disposing an analyzer device in the optical axis between the article and the sensor;

disposing a phase compensator device in one of said optical axes for compensating the phase shift between the P-plane component and the S-plane component caused by one of said materials; and rotating at least two of said polarizer, analyzer and phase compensator devices around the corresponding optical axes to obtain the maximum contrast between the two materials in an image of said article formed responsive to light collected by said sensor.

2. The method according to claim 1, wherein the maximum contrast is obtained by rotating two of said devices while holding the third device fixed to minimize the intensity of one of said materials in the image.

3. The method according to claim 2, wherein the angle of incidence of the light on the article is selected to obtain maximum contrast.

4. The method according to claim 2, wherein the angular coverage of the light emitted by said source is selected to minimize the effect of surface relief on the contrast in the image.

5. The method according to claim 1, wherein the central wavelength of the light emitted by said source is selected to obtain maximum contrast between the two materials in the image.

6. The method according to claim 5, wherein the spectral bandwidth of the light emitted by said source is selected to obtain substantially uniform contrast in the image over the field of view.

7. The method according to claim 1, wherein for a preselected rotational position of any two of said devices, the intensity of the light collected from at least one of said materials is measured to provide an indication of the thickness of the structure of the respective material or of its index of refraction.

8. The method according to claim 1, wherein said illuminated article has a reflecting surface, and said sensor collects light reflected from said article.

9. The method according to claim 1, wherein said article is transparent, and said sensor collects light having passed through said article.

10. The method according to claim 1, wherein said phase compensator device is in the optical path between said polarizer and said article.

11. The method according to claim 1, wherein said phase compensator device is in the optical path between said article and said analyzer.

12. The method according to claim 1, wherein at least one of said polarizer device and said analyzer device are dichroic sheets.

13. The method according to claim 1, wherein said phase compensator device is a mica quarter-wave plate.

14. The method according to claim 1, wherein said phase compensator device is a liquid crystal quarter-wave plate.

15. The method according to claim 1, wherein said light sensor includes a linear array of light sensitive elements, which is scanned with respect to said article along a line perpendicular to the array of light sensitive elements.

16. The method according to claim 15, wherein said planar array of light sensitive elements is disposed in a plane which is inclined with respect to the plane of the scanned article, such that the array of elements lies within focus with respect to the object.

17. The method according to claim 1, wherein said light sensor includes a planar array of light sensitive elements, which is scanned with respect to the article to be inspected in a step-by-step manner.

18. A method of optically measuring the variation in thickness or index of refraction of a thin film structure, comprising the steps of:
illuminating the structure with light, collecting the light leaving the structure so illuminated using a light sensor, and measuring the grey level signal of the image, characterized by the further steps of:
disposing a polarizer device in the optical axis between the source and the structure, for linearly polarizing the incident light to have a P-plane component parallel to the plane of incidence of said light, and an S-plane component perpendicular to the P-plane, disposing an analyzer device in the optical axis between the structure and the sensor, and disposing a phase compensator in one of said optical axes for compensating the phase shift between the P-plane component and the S-plane component caused by said thin film structure;
selecting a reference point on the article surface;
rotating said polarizer, analyzer and phase compensator devices around their optical axes to obtain a minimum grey level signal in said preselected reference point; and
determining the thickness or index of refraction of said thin film structure responsive to the measurement of the grey level signal.

19. Apparatus for automatically inspecting the surface of an article particularly a thin film multilayer structure including at least two materials, comprising:
illumination means including an intense source of polychromatic light of wide spectral range for illuminating the article with incident light;
a light sensor for collecting light leaving the article and for outputting electrical signals varying responsive to the intensity of the collected light;
imaging means for optically imaging the illuminated article responsive to the light collected by the light sensor; and
processing means for processing the output of said light sensor in order to indicate defects in said article;
said illumination means including:
a polarizer device for linearly polarizing the incident light, so as to include a P-plane component parallel to the plane of incidence of said light, and an S-plane component perpendicular to the P-plane;
said imaging means including:
an analyzer device for extinguishing the reflected light;
said apparatus including:
a phase compensator device for compensating the phase shift between the P-plane component and the S-plane component caused by one of said materials, disposed in the optical axis of said illumination means between the polarizer and the article or in that of said imaging means between the article and the analyzer; and
means for rotating at least two of said polarizer, analyzer, and phase compensator devices, to obtain the maximum contrast between the two materials in the image of the article.

20. The apparatus according to claim 19 wherein said means for rotating rotates two of said polarizer, analyzer and phase compensator devices about the optical axes of said illumination means or said imaging means, while maintaining the position of the third of said devices constant, to minimize the light intensity received by said light sensor responsive to the said materials.

21. The apparatus according to claim 19, further including means for selecting the central wavelength of the light emitted by the source to obtain maximum contrast.

22. The apparatus according to claim 19, further including means for selecting the spectral bandwidth of the incident light to obtain substantially uniform contrast over the field of view.

23. The apparatus according to claim 19, further including means for selecting the angle of incidence of the incident light on the article to obtain maximum contrast.

24. The apparatus according to claim 19, further including means for selecting the angular coverage of the incident light in order to minimize the effect of surface relief on contrast.

25. The apparatus according to claim 19, further including means for measuring the intensity of the light collected from at least one of said materials, after determining the angle of rotation of polarization producing the minimal light intensity in the image responsive to said one material, to provide an indication of variation in the thickness of the structure of the respective material or of its index of refraction.

26. The apparatus according to claim 19, wherein said article to be inspected has a reflective surface, and wherein said illuminating means and said light sensor are disposed on the same side of the article so that said sensor optically collects light reflected from the article.

27. The apparatus according to claim 19, wherein said article to be inspected is transparent, and wherein said light sensor and said illuminating means are disposed on opposite sides of said article, whereby the sensor collects the light transmitted through the article.

28. The apparatus according to claim 19, wherein said phase compensator device is disposed in the optical axis of said illumination means between the polarizer and said article.

29. The apparatus according to claim 19, wherein said phase compensator device is disposed in the optical axis of said imaging means between said article and said analyzer.

30. The apparatus of claim 19, further including storage means for storing optical parameters of the illuminating means to be varied in order to maintain maximum contrast in the image, and processor means for automatically varying the angles of rotation of said at least two polarizer, analyzer and compensator devices to obtain the maximum contrast in the examination of articles of specific materials, according to the stored parameters.

31. The apparatus according to claim 19, wherein at least one of said polarizer and said analyzer device is a dichroic sheet.

32. The apparatus according to claim 19, wherein said phase compensator is a mica quarter-wave plate.

33. The apparatus according to claim 19, wherein said phase compensator is a liquid crystal quarter-wave plate.

34. The apparatus according to claim 19, wherein said light sensor includes a linear array of light sensitive elements, which is continuously scanned with respect to the article along a line perpendicular to the linear array of light sensitive elements.

35. The apparatus according to claim 19, wherein said light sensor includes a planar array of light sensitive elements, which is scanned with respect to the article in a step-by-step manner.

36. The apparatus according to claim 35, wherein said imaging means includes means for focusing light from the article onto the sensor, and wherein said planar array of light sensitive elements is disposed in a plane which is inclined with respect to the plane of the scanned structure, such that the entire array of elements lies in the depth of focus of image obtained from the object.

* * * * *